(12) United States Patent
Ghatak

(10) Patent No.: US 10,788,482 B2
(45) Date of Patent: Sep. 29, 2020

(54) IMMUNIZATION TESTING SYSTEM

(71) Applicant: ImmunoProfile, LLC, East Brunswick, NJ (US)

(72) Inventor: Sudip Ghatak, East Brunswick, NJ (US)

(73) Assignee: IMMUNOPROFILE, LLC, East Brunswick, NJ (US)

( * ) Notice: Subject to any disclaimer, the term of this patent is extended or adjusted under 35 U.S.C. 154(b) by 18 days.

(21) Appl. No.: 15/599,775

(22) Filed: May 19, 2017

(65) Prior Publication Data

US 2017/0322203 A1 Nov. 9, 2017

Related U.S. Application Data

(62) Division of application No. 14/360,763, filed as application No. PCT/US2012/066226 on Nov. 21, 2012, now abandoned.

(60) Provisional application No. 61/563,887, filed on Nov. 28, 2011.

(51) Int. Cl.
  *G01N 33/53* (2006.01)
  *G01N 33/68* (2006.01)
(52) U.S. Cl.
  CPC ......... *G01N 33/53* (2013.01); *G01N 33/6854* (2013.01)
(58) Field of Classification Search
  None
  See application file for complete search history.

(56) References Cited

U.S. PATENT DOCUMENTS

| | | | |
|---|---|---|---|
| 5,869,004 A | 2/1999 | Parce et al. | |
| 5,961,800 A | 10/1999 | McBride et al. | |
| 5,976,896 A | 11/1999 | Kumar et al. | |
| 5,992,820 A | 11/1999 | Fare et al. | |
| 6,106,685 A | 8/2000 | McBride et al. | |
| 6,109,717 A | 8/2000 | Kane et al. | |
| 6,937,991 B1 | 8/2005 | Zompa et al. | |
| 7,132,078 B2 | 11/2006 | Rawson et al. | |
| 7,476,361 B2 | 1/2009 | Kellogg et al. | |
| 7,635,594 B2 | 12/2009 | Holmes et al. | |
| 7,763,453 B2 | 7/2010 | Clemmens et al. | |
| 7,908,155 B2* | 3/2011 | Fuerst | G06F 19/3418 705/3 |
| 8,498,879 B2 | 7/2013 | Michon et al. | |
| 2002/0150884 A1 | 10/2002 | Zmuda et al. | |
| 2003/0143652 A1 | 7/2003 | Simonson | |
| 2004/0229378 A1 | 11/2004 | Schulte et al. | |
| 2005/0009011 A1 | 1/2005 | Zmuda et al. | |
| 2005/0065817 A1* | 3/2005 | Mihai | A61B 5/0002 705/2 |
| 2005/0227370 A1 | 10/2005 | Ramel et al. | |
| 2005/0249633 A1 | 11/2005 | Blatt et al. | |
| 2006/0264782 A1 | 11/2006 | Holmes et al. | |
| 2007/0081920 A1 | 4/2007 | Murphy et al. | |
| 2007/0189921 A1* | 8/2007 | Duong | G01N 21/6452 436/149 |
| 2007/0224084 A1* | 9/2007 | Holmes | A61B 5/1411 422/68.1 |
| 2008/0019866 A1 | 1/2008 | Paek et al. | |
| 2008/0059534 A1 | 3/2008 | Stroman et al. | |
| 2008/0314325 A1 | 12/2008 | Hempstead et al. | |
| 2009/0298059 A1 | 12/2009 | Gumbrecht et al. | |
| 2009/0299767 A1* | 12/2009 | Michon | G06Q 50/22 705/3 |
| 2011/0150705 A1* | 6/2011 | Doyle | B01L 3/5055 422/82.02 |
| 2012/0071342 A1* | 3/2012 | Lochhead | G01N 21/6452 506/9 |
| 2013/0137607 A1 | 5/2013 | Ghatak | |
| 2014/0072959 A1 | 3/2014 | Determan et al. | |
| 2014/0323347 A1 | 10/2014 | Ghatak | |

FOREIGN PATENT DOCUMENTS

WO   2013081933 A1   6/2013

OTHER PUBLICATIONS

Wicker et al. J. Lab. Med. 2009 33: 223-227 (Year: 2009).*
Louisirirotchanakul et al., "HBsAg Diagnostic Kits in the Detection of Hepatitis B Virus Mutation within "a" Determinant", Viral Immunology, vol. 19, Issue 1, pp. 108-114, Mar. 1, 2006.
Gonçalves et al., "Levels of Diphtheria and Tetanus Specific IgG of Portuguese Adult Women, Before and After Vaccination With Adult Type Td. Duration of Immunity Following Vaccination", BMC Public Health Biomed Central London, GB, vol. 7, Issue 1, pp. 109, Jun. 12, 2007.
Wicker et al., "Sind Medizinstudenten Ausreichend Geimpft? / Are Medical Students Sufficiently Vaccinated?", Laboratoriumsmedizin, vol. 33, Issue 4, pp. 223-227, Jan. 1, 2009.
Zengin et al., "Humoral Immunity to Diphtheria, Tetanus, Measles, and Hemophilus Influenzae Type B in Children With Acute Lymphoblastic Leukemia and Response to Re-Vaccination", Pediatr Blood Cancer, vol. 53, Issue 6, pp. 967-972, Dec. 1, 2009.
Louisirirotchanakul et al., "Comparison of the Technical and Clinical Performance of the Elecsys HBsAg II Assay With the Architect, AxSym, and Advia Centaur HbsAg Screening Assays", Journal of Medical Virology, vol. 82, Issue 5, pp. 755-762, May 1, 2010.

(Continued)

*Primary Examiner* — Changhwa J Cheu
(74) *Attorney, Agent, or Firm* — Carter, DeLuca & Farrell LLP

(57) ABSTRACT

A point of care immunization system based upon microfluidics and microtitration technologies to rapidly test a patient in order to ascertain an immunization profile so that vaccinations can be administered to address identified gaps. A point of care system comprised of uniquely shaped and color distinguishing sample and test cartridges, with said test cartridges configured to meet healthcare requirements of national governing bodies. A point of care system including an easy access vaccine storage device with indicators to provide data on viability of stored vaccines.

22 Claims, 9 Drawing Sheets

(56) References Cited

OTHER PUBLICATIONS

Bian et al., "Development of Retinol-Binding Protein 4 Immunocolloidal Gold Fast Test Strip Using High-Sensitivity Monoclonal Antibodies Generated by DNA Immunization", Acta Biochimica Et Biophysica Sinica, vol. 42, Issue 12, pp. 847-853, Nov. 9, 2010.
Extended European Search Report dated Jan. 19, 2016 for Application No. 12853252.0.
Sabine Wicker et al., Sind Medizinstudenten ausreichend geimpft? Are medical students sufficiently vaccinated?, LaboratoriumsMedizin, vol. 22, No. 4, Jan. 1, 2009 (Jan. 1, 2009), pp. 223-227.
Chinese Office Action issued in Chinese Application No. 201580044039.6 dated Apr. 10, 2018.
Extended European Sarch Report issued in EP 15812022.0/1408 dated Nov. 20, 2017.
Glynn et al., "CD4 Counting Technologies for HIV Therapy Monitoring in Resource-Poor Settings-State-of-the-Art and Emerging Microtechnologies", Lab on a Chip, vol. 13, Issue 14, pp. 2731-2748, Jul. 21, 2013.
Chin et al., "Low-Cost Microdevices for Point-of-Care Testing", Point of Care Diagnostics on a Chip, Springer-Verlag Berlin Heidelberg, ISBN 978-3-642-29268-2, pp. 3-21, 2013.
International Seach Report and Written Opinion dated Oct. 14, 2015 for PCT Application No. PCT/US2015/037067.
Centers for Disease Control, www.cdc.gov/vaccines/programs/iis/about.html, pp. 1-3, Date May 15, 2012.
Control, www.cdc.gov/vaccines/adults/vaccination-records.html, pp. 1-3. Date Jan. 25, 2013.
Canadian Office Action issued in Canadian Application No. 2,890,892 dated Jan. 8, 2019, 6 pages.
Canadian Office Action dated Nov. 15, 2019, corresponding to counterpart Canadian Application No. 2,890,892; 4 pages.
U.S. Office Action dated Jul. 30, 2020 in connection with U.S. Appl. No. 15/978,751; 14 pages.

* cited by examiner

| Vaccine Targets | | | | | | | | | | |
|---|---|---|---|---|---|---|---|---|---|---|
| | Hep B | Rota-virus | DTP | Haemop hilus | Pneumocc ocal | Polio | Influen za | MMR | Varic ella | Hep A |
| 1:10 | | | | | | | | | | |
| 1:100 | | | | | | | | | | |
| 1:1000 | | | | | | | | | | |
| 1:10,000 | | | | | | | | | | |
| 1:100,000 | | | | | | | | | | |
| Control | | | | | | | | | | |

(Sample Dilutions)

IMMUNIZATION TESTING SYSTEM

CROSS-REFERENCE TO RELATED APPLICATIONS

This application is a divisional of U.S. patent application Ser. No. 14/360,763, filed May 27, 2014, which is the U.S. National Phase of PCT Application Ser. No. PCT/US2012/066226, filed Nov. 21, 2012, which claims the priority of U.S. Provisional Application Ser. No. 61/563,887, filed Nov. 28, 2011.

FIELD

The present invention relates to, among other things, a system to diagnose a patient's immunization protection levels which is comprised of three elements: a point of care diagnostic instrument, targeted test cartridges and accompanying vaccine supply packs.

The point of care diagnostic instrument measures the antibody levels for various targets based upon a patient's sample. The targeted test cartridge is configured with the necessary immunization tests per the healthcare guidelines of the specific country for the appropriate group by age, gender, life changing event, and the like. The accompanying vaccine supply pack is configured with vaccines corresponding to the targeted test cartridge, offering the needed vaccinations based upon the patient's test result. The system also updates the patient's immunization records and links to the appropriate electronic patient records, laboratory information system, hospital information system and insurance reporting system, among others.

Various types of point of care devices and systems have been proposed. For example, U.S. Pat. No. 7,635,594 to Holmes et al. discloses a device for real-time data transmission between a patient and medical practitioners to facilitate high throughput point-of-care testing in detection of disease-indicative analytes including immuno-assays from various bodily fluids. Point of care diagnostic instruments have been employed for years in medical offices and clinical settings to target various applications. Typically point of care instruments are targeted at rapid testing to detect a patient's exposure to an infectious agent or to provide general information on vital statistics such red blood cell count, white blood cell count and amount of lead present. Infectious disease tests include situations such as determining the presence of streptococcal (strep) bacteria in diagnosing strep throat. Many of these tests fall in the category of CLIA (Clinical Laboratory Improvement Amendments) waived tests, which are defined as simple laboratory examinations and procedures that are cleared by the Food and Drug Administration (FDA) for home use; employ methodologies that are so simple and accurate as to render the likelihood of erroneous results negligible; or pose no reasonable risk of harm to the patient if the test is performed incorrectly.

The main problem is that no point of care device exists to quickly and inexpensively detect a patient's antibody levels to determine immunization protections. Currently, to make such a diagnosis the patient must have blood drawn at a clinical setting and the blood sample tested in a clinical laboratory. The tests are ordered on an individual basis, such as measles, and can take more than a week for response time at high "per test" costs. If a patient needs to be tested for multiple immunization levels, separate and individual tests must be ordered. There is no availability to quickly diagnose a patient's immunity level across the recommended healthcare guidelines in an easy, rapid and cost effective manner. Furthermore, poor record tracking of individual patient's immunizations can result in patients themselves generally not knowing if they are protected.

The range of vaccine efficacies is wide—some as low as 50%, especially in patients with compromised immune systems, and there is no way to know how an individual will respond to the vaccine. Not only is the duration of protection unpredictable, but other factors can affect a vaccine's efficacy, including missed booster shots, a change in medical condition (HIV, hepatitis, obesity), age of vaccinations, age of vaccines, compromised vaccines, or the like. Certain vaccines cannot be given to children or pregnant women, or while a patient is immuno-compromised.

If a patient is administered an old or even expired vaccine, the patient may not receive full immunity. Recalls occasionally pull out problem vaccine batches, but they are not a guarantee that all vaccines are viable and effective.

Another growing problem is that patients are opting out of vaccines, so communities no longer have near 100% immunization rates. This leads to disease outbreaks in the US and other developed countries when a disease carrier enters a vulnerable population. Disease outbreaks for measles and whooping cough have occurred in the US in 2011, along with outbreaks in Europe. Given the ease of travel from vast geographies, a disease carrier can travel almost anywhere in the world in less than twenty-four hours. The only available testing for immunity is costly for the patient, and does not yield immediate results.

A simple but effective solution is needed to enable patients and the healthcare provider the means to quickly test for immunization protection and address any identified gaps through the timely administration of the necessary vaccines. The system needs to be easy to use, timely and targeted. It should comprise of a simple to use diagnostic instrument with ports for the sample and the targeted test cartridge. Target test cartridges are for example designed following the recommended guidelines for each country, and are for example adapted for a range of parameters such as age, gender and life changing event. The system should provide timely test results to identify the gaps in the immunization profile and quickly fill the gaps with the timely administration of the necessary vaccine(s). The system should also have a means to update and track patient's immunization records linking it to clinical information systems and providing an electronic/paper copy to the patient.

Conventional point of care devices are better suited for disease detection and measure vital parameters from blood and other bodily fluids. Currently no point of care device is targeted for detecting immunization levels leaving most patients unclear of how well they are protected against disease until disease sets upon them.

This invention is, in general, to diagnose anti-body levels for immunity levels, using a point of care diagnostic device, targeted test cartridges, corresponding vaccine supply packs, sensors for temperature, sensors of expiry, tags to establish pedigree and smart chips to instruct test protocols.

SUMMARY OF THE INVENTION

The present invention is directed to the diagnosis of antibody levels in a patient's sample to determine a patient immunization protection levels or allergy indicative IgE levels. (Any reference herein to "immunization testing" includes allergic IgE testing.) The invention is comprised of cartridges, including targeted test cartridges, with controls so that two distinct cartridges cannot be mistaken for each other. The targeted test cartridge can be configured with the necessary immunization tests per the healthcare guidelines of the specific country for the appropriate group by age, gender, life changing event, and the like. The targeted test cartridge can include a smart chip (e.g., transponder) or bar code to instruct the point of care diagnostic device to initiate the appropriate test protocols. The corresponding vaccine supply packs can be configured to the targeted test cartridge so that in the event a gap is identified in the immunization profile, the appropriate vaccine can be administered in a timely manner. The vaccine supply pack can organize the vaccine vials in an easy to store and access manner. The supply pack can include sensors for temperature detection in the event the vaccines were compromised due to refrigeration malfunction or power outages. The supply pack can include sensors providing warnings in the event a vaccine has passed its expiration preventing its use, and communication hardware for linking the sensors to supply/inventory management systems. The supply pack can also incorporate tags (IDs) such RFID (radio-frequency identification) or bar codes to establish vaccine pedigree to prevent them from being compromised or counterfeited. In certain embodiments, the invention provides a new and improved point of care testing device to detect antibody levels per immunization protection.

In certain embodiments, the invention provides a biological sample cartridge for ease of use and prevents confusion with the targeted test cartridge. The biological sample cartridge may contain anti-coagulants in the case of blood samples to facilitate the sample prep process, enable easier transfer of the blood sample and improve assay performance.

In certain embodiments, the invention provides a targeted test cartridge customized to the meet the healthcare requirements for specific countries across age, gender and life changing events among others.

In certain embodiments, the invention provides a vaccine supply pack providing ease of use, ease of access, organized storage, space saving, sensors to detect temperature, coding to indicate expiration, sensor to detect quantities/supply, tags to establish pedigree, and the like.

In certain embodiments, the invention provides a means to supply the healthcare provider's patient with the necessary vaccine to fill any gaps in their individual immunization profile.

In certain embodiments, the invention provides a method for updating a patient's immunization record for the clinical information systems and patient's personal records.

Provided is an immunization testing device for testing a biological sample from a subject comprising: an analytical module adapted to make two or more dilutions a fluid that is or is derived from the biological sample, contact said dilutions with separate replicates of vaccine- or sensitization-indicative antigens so as to generate a signals indicative of the amount of antigen-reactive immune molecules in the biological fluid dilutions.

Provided is an immunization testing device for testing a biological sample from a subject comprising, an analytical module comprising fluidic pathways for conducting dilutions, a controller, an data output device, and one or more input ports having a conjugate input comprising a test cartridge, wherein one or more of the following obtains:
wired connectivity; wireless connectivity; interfaces with hospital/clinical information systems; interfaces with laboratory information systems; provides wired and wireless printer ports; provides links to electronic patient records; provides self-maintenance (e.g., via diagnostic hardware and software for the instrument and/or the cartridges); provides links to smart phones, PDAs printers, and the like; provides biological fluid sample cartridges with:
unique shape and/or distinguishable color;
ability to supply needed sample for assay; provides targeted test cartridges with
unique shape and/or distinguishable color and/or ability to supply needed antigens for assay and/or chip to instruct instrument to initiate protocols and/or configured to meet testing requirements as set by healthcare governing bodies and/or individual chambers for each vaccine target with requisite antigen; provides vaccine supply pack with
compact storage for vaccines and/or easy access and/or small profile saving space in refrigerator and/or smart sensors to indicate temperature and/or smart sensors to indicate expiration date and/or smart sensors to indicate vaccine supply and/or linkages to supply management and ordering systems and/or radio frequency tags to establish pedigree and/or bar code tags to establish pedigree; provides smart app with
smart phones and computer devices; ability to track and update personal immunization records; ability to share personal immunization records provides business model for selling vaccines with
companion diagnostic system for vaccines and/or means for identifying gaps in a person's immunization profile and/or administering only necessary vaccines and/or charging a service or handling fee for vaccine administration and/or charging a fee for the vaccination itself.

Also provided is an immunization testing device for testing a biological sample from a subject comprising, an analytical module comprising a controller, an data output device, and one or more input ports having a conjugate input comprising a test cartridge port, wherein the test cartridge port has an ID receiver for receiving an ID from a immunization test cartridge, wherein the controller is adapted to operate the analytical module to make two or more dilutions of the biological sample, contact said dilutions with separate replicates of vaccine- or sensitization-indicative antigens so as to generate a signals indicative of the amount of antigen-reactive immune molecules in the biological dilutions, interpret the received ID to identify one of a pre-set plurality of available immunization test cartridges, and to utilize the generated signals and the immunization test cartridge to output a report on the immune status of the subject with respect to an array of separate vaccine- or sensitization-indicative antigens (e.g., 4 or more). The ports can be shaped to accept their conjugate input and not accept the conjugate inputs of other ports present. The biological sample cartridge may contain anti-coagulants in the case of blood samples to facilitate the sample prep process, enable easier transfer of the blood sample and better assay performance. The first step of the immunoprofile assay is a sample prep step to ensure the blood sample is properly managed in order to serve the purposes of the assay. Part of this effort can be, as needed, to treat the blood sample with anti-coagulant to prevent the blood from clotting which in some instances can have negative effects on the assay process.

In certain embodiments, the controller is adapted to operate with (A) a collection of immunization test cartridges comprising reagents for testing immune status against an array of vaccine- or sensitization-indicative antigens, the collection including two or more cartridges for testing separate arrays of vaccine- or sensitization-indicative antigens, the separate arrays adapted for use with separate patient populations, the cartridges having IDs that are distinctive of the separate arrays, wherein the controller reads the ID of a given utilized test cartridge and presents the output report correlating the vaccination status results with the respective vaccine- or sensitization-indicative antigens based on the read ID. In one embodiment, the controller is adapted to operate with packs of immunization compositions, separate packs matching the separate arrays of the immunization test cartridges (vaccines matching the vaccine-indicative antigens), the distinct immunization compositions identifiably spatially segregated on the packs, the packs having IDs that are distinctive of the separate arrays of immunization compositions, wherein after presenting an output report the controller compares the ID of a presented pack with the ID of the utilized test cartridge to confirm that the cognate pack has been presented. In one embodiment, the controller is adapted to operate with packs of immunization compositions, separate packs matching the separate arrays of the immunization test cartridges; wherein after presenting an output report the controller compares an ID of a presented immunization composition with the output report data to confirm that the immunization composition matches the tested vaccine-indicative antigens. In another embodiment, the controller further confirms that the presented immunization composition matches a vaccine-indicative antigen found to have a deficient immune response.

In certain embodiments, the immunization testing device takes the form of a handheld sampling device, as described below. In certain embodiments, the vaccine indicative antigens are arrayed on a test strip adapted to contact the dilutions by flow of the dilution material through columns of the test strip so as to serially contact the antigens. In certain embodiments, the test strips are incorporated into the immunization test cartridges.

Also provided is a collection of immunization test cartridges comprising reagents for testing immune status against an array of vaccine- or sensitization-indicative antigens, the collection including two or more cartridges for testing separate arrays of vaccine- or sensitization-indicative antigens, the separate arrays adapted for use with separate patient populations, the cartridges having IDs that are distinctive of the separate arrays. Further provided is a kit comprising (A) a collection of immunization test cartridges, and (B) packs of immunization compositions, separate packs matching the separate arrays of the immunization test cartridges, the distinct immunization compositions identifiably spatially segregated on the packs, the packs having IDs that are distinctive of the separate arrays of immunization compositions, the collections and packs adapted to be operative with an analytical module that utilizes the immunization test cartridges to provide subject immune statuses for the antigens of given immunization test cartridges, and which compares the ID of a utilized immunization test cartridge and that of a presented pack to confirm that the cognate pack has been presented.

In certain embodiments, the immunization composition packs comprise a temperature sensor, electronic memory for tracking temperature from the sensor over time, and wherein the packs are adapted to communicate the temperature tracking to the analytical module. In certain embodiments, the immunization test cartridges are in the form of handheld sampling devices.

Further provided is a method of operating the testing device, comprising operating the testing device with a biological sample from a patient utilizing an immunization test cartridge, and thereby outputting a report on the immune status of the subject with respect to an array of separate vaccine- or sensitization-indicative antigens. Also provided is a method of operating the testing device operative with an immunization pack ID reader, comprising operating the testing device with a biological sample from a patient utilizing a said immunization test cartridge, and thereby outputting a report on the immune status of the subject with respect to an array of separate vaccine- or sensitization-indicative antigens; presenting a said immunization pack to the immunization pack ID reader to generate output from the testing device confirming or negating that the immunization pack is the cognate of the test cartridge. The method can further include the controller obtaining from the immunization pack information on immunization stock, calculating the further utilization implied by the immune status report, and, if needed based on this data, generating (i) a report identifying vaccine restocking needs or (ii) a purchase order to a vaccine supplier. The report or purchase order can also be sent by the controller to a user or to the vaccine supplier, such as by email or fax.

Also provided is a method of operating the testing device with an immunization composition ID reader, comprising operating the testing device with a biological sample from a patient utilizing a said immunization test cartridge, and thereby outputting a report on the immune status of the subject with respect to an array of separate vaccine- or sensitization-indicative antigens; presenting a said immunization composition to the immunization composition ID reader to generate output from the testing device confirming or negating that the immunization composition is the immunization composition called for by the immune status report. In certain embodiments of the method, the analytical module is comprised in a handheld sampling device.

The above methods can be conducted at the point-of-care, such as a physician's office, clinic, patient bedside, and the like.

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

These and other features and advantages of embodiments the present invention will be fully apparent from the following description, when taken in connection with the included drawings.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

Figure 1:
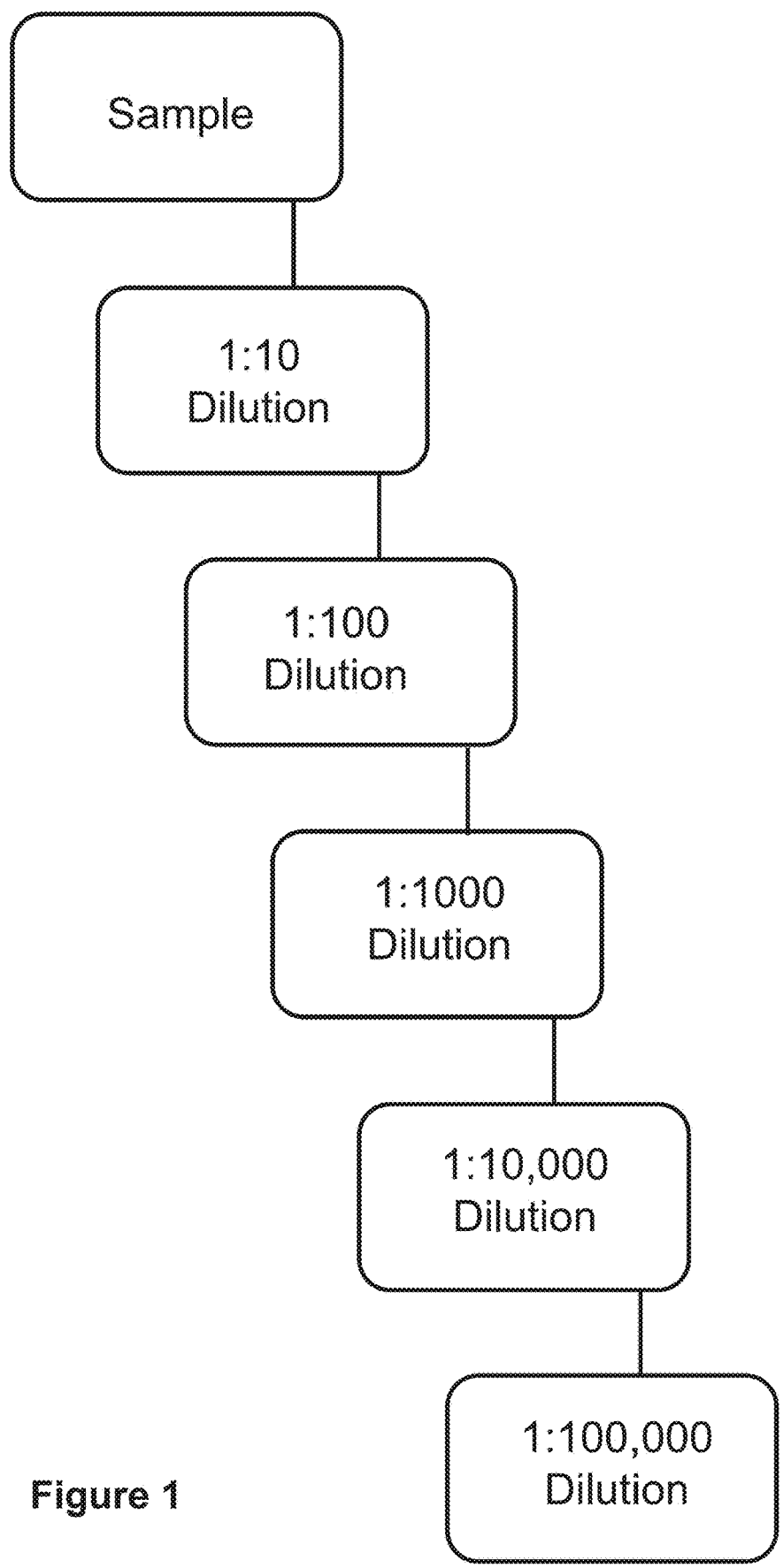
FIG. 1 is a detailed view of sample dilution profile.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation. For examples, elements and features can be shared between various embodiments that may operate at atmospheric pressure, or higher pressures, depending on among other things the feedstock natural gas pressure available at different locations of the device.

DETAILED DESCRIPTION OF THE INVENTION

Referring now to the drawings in greater detail, FIG. 1 shows a detailed view of an exemplary sample dilution profile. The sample from the patient will be diluted per the protocols of the test procedure, typically in series fashion. Using fluidic devices (such as microfluidics or robotic pipetting) the sample can be mixed with dilution buffer solution to create the first dilution (e.g. 1:10) which is one part sample and nine parts buffer. The same or alternative dilutions can be conducted on dilutions of a given dilution step. In the Figure we illustrate a simple dilution system, but the point of care device can make virtually any dilution pool by taking the appropriate amount of sample combined with the specified amount of buffer. The figure is only an illustration of one such dilution profile.

The biological sample can be a fluid (e.g., blood, sera, lymph fluid, urine, tears, saliva or the like), a tissue (such as marrow, hair follicles, or the like). In the case of non-fluids, antibodies are extracted. The sample can be from a human, or from any animal with an immune system, such as a dog, cat, horse, donkey, elephant, manatee, In the diagnostic method conducted in the immunization testing device, dilutions are contacted with the respective vaccine- or sensitization-indicative antigens (or control antigens) and the ancillary agents used to develop a signal indicative of the amount of antibody responsive to the antigen that is present. These ancillary agents can be antibodies, color-developing reagents (inclusive of fluorescence-developing reagents), and the like. Fluorescence can include FRET, wherein fluorescence transfer between two assay moieties enhances signal-to-noise. The diagnostic method (assay) will typically at some point fix the signal on a surface to provide a way of concentrating signal and washing away reagent that might provide false signal. The vaccine- or sensitization-indicative antigen can be provided fixed to the surface, or can be fixed during the course of the diagnostic method. The assay can be a competitive assay, in which a diminution of signal is indicative of unlabeled antibody from the biological sample competing out labeled antibody. Or, the assay can provide a positive correlation between experimental antibody amount and signal, such as via a sandwich assay. In this case, for example, label can be on antigen, on reagent antibody, or the like. Label can be directly measurable, or be the means for developing a measurable signal, such as by being reactive with a binding moiety (e.g., antibody, lectin) having a further label, or by having an attached enzyme.

A given dilution can be assayed against different antigens in separate compartments, or can be assayed such that the signals for the different antigen localize in different places. For example, where the antigen is labeled, it might be captured by different non-competitive antibody localized separately from the capture antibodies for other antigens. Or the antigen can be separately localized on a solid. For example, separate, identifiable beads or other solids can be incubated with the dilution to provide separate signals, or signal can be spatially resolved on a surface. Immunochromatographic methods (lateral flow) can be used to move reagents over the detection surface and provide washing. In lateral flow, reagents can be provided dry on a portion of a surface, and be solubilized and caused to flow over the signal-generating portion. In certain embodiments, diluted biological can be delivered to an absorbent region, providing a reservoir of fluid for lateral flow.

In certain embodiments, the dilution and/or the presentation and/or removal of reagents for developing signal are delivered robotically, for example using pipetting methods.

The methods and devices of the invention are adapted to facilitate assaying for a substantial set (e.g., four or more) of vaccination statuses in one relatively quick operation beginning with drawing a biological sample. This set can be termed a "diagnosis set." Test cartridges are adapted to provide the all of the vaccine- or sensitization-indicative antigens of a given set. Sets are designed to be particularly useful for particular populations. For example, one set is used for preschoolers, another for male teens, another for female teens, another for travelers to a given region, and the like.

Figure 6:
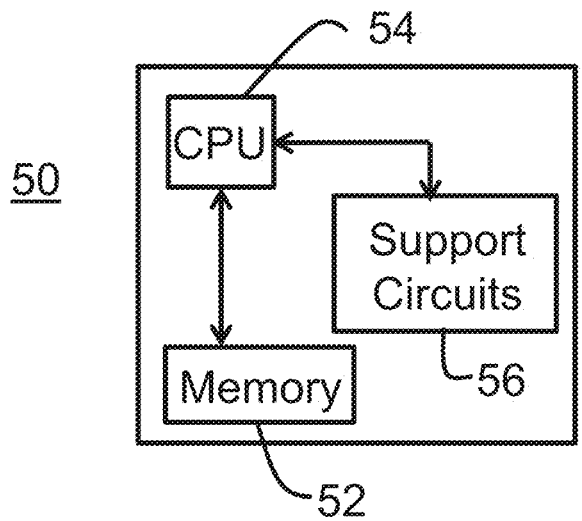
FIG. 6 shows a controller that can be incorporated into the analytical module.

The analytical module can contain a controller 50 (FIG. 6), which comprises a central processing unit (CPU) 54, a memory 52, and support circuits 56 for the CPU 54 and is coupled to and controls the various elements of the immunization testing device or, alternatively, operates to do so in conjunction with computers (or controllers) connected to the immunization testing device. For example, another electronic device can supply software, or operations may be calculated off-sight with controller 50 coordinating off-sight operations with the local environment. The controller 50 may be one of any form of general-purpose computer processor that can be used for controlling various devices and sub-processors. The memory, or computer-readable medium, 52 of the CPU 54 may be one or more of readily available memory such as random access memory (RAM), read only memory (ROM), flash memory, floppy disk, hard disk, or any other form of digital storage, local or remote. The support circuits 56 are coupled to the CPU 54 for supporting the processor in a conventional manner. These circuits can include cache, power supplies, clock circuits, input/output circuitry and subsystems, and the like. Methods of operating the immunization testing device may be stored in the memory 52 as software routine that may be executed or invoked to control the operation of the immunization testing device 100. The software routine may also be stored and/or executed by a second CPU (not shown) that is remotely located from the hardware being controlled by the CPU 54. While the above discussion may speak of the "controller" taking certain actions, it will be recognized that it may take such action in conjunction with connected devices.

In certain embodiments, the controller is a smart phone, tablet, PC or the like that connects to the analytical module by wire connections or wirelessly.

In certain embodiments certain of the logic circuits or algorithms may be distantly external, such as in Canada. In such embodiments the "controller" is made up of the electronic elements at or near the point-of-care that coordinate data going to such distant logic circuits and operative instructions derived from such distant logic circuits.

In collecting the sample, either via the sample cartridge, test cartridge or a conventional collection tube, the collection will generally be labeled with patient identifying information. It may be that the labeling will be via a microchip or matrix code (2D bar code) that is rich in information. Thus, a data input device for the immunization testing device can be a scanner for this data rich information.

The immunization testing device may be adapted to operate in conjunction with one or a variety of devices utilized with electronic medical records, such as i-Pads, Android devices, i-Phones, laptops, and the like. In this manner, associating the testing with patient information can be facilitated, and data that must be keyboarded in (or voice to text converted) or can be inputted with a device that is better optimized for these functions. Even where significant data input and output is done via an linked device, it can be useful to have an output screen of the device, since after initiation it may prove convenient for the associated medical records device to be used with another patient in another room. More immediate input tools can also be useful, such as just a few buttons whose functions change with the circumstances as announced by for example an adjacent portion of an output screen.

Thus, the output device of the immunization testing device can be a wire output (e.g., USB), or a wireless transmitter (e.g., Bluetooth).

The test cartridge(s) are preferably one test cartridge, but in certain embodiments two or more test cartridges are used. The test cartridge(s) provide the consumable analytical reagents, and may include dilution fluid (e.g., should such not be presented by a biological sample cartridge). In certain embodiments, the test cartridge(s) provide all sample contacting materials, such as disposable pipet tips, or fluidic pathways, or reaction wells, or the like, or all such elements used downstream of biological sample dilution. Inputs (such as a test cartridge) into the analytical module can have a unique shape (such as guide features) such that it can only be connected to its cognate port. Such inputs and the port can be marked with a shared, otherwise unique color or symbol to facilitate quick connection to the correct port.

In certain embodiments, all the reagents, including the vaccine- or sensitization-indicative antigens of a diagnosis set, are provided on one test cartridge. Other test cartridges may be used to provide reagents that do not vary across analyses of diagnosis sets.

In certain embodiments, inputs or other components have IDs, which are symbols, codes (such as linear or multi-dimensional bar codes), devices responsive to electromagnetic queries to emit an electromagnetic identifier (e.g., RFID devices), circuit boards (which may connect via electrical contacts or wirelessly) or the like that can be read by reading devices on the analytical module. An ID receiver can be, among other things, electrical contacts. In this embodiment, the testing device's controller reads the ID(s) and utilizes the information as needed for conducting the analytical processing and reporting. It may be that the same processing steps are conducted for all test cartridges and all vaccine- or sensitization-indicative antigens, in which case the ID information may inform the report generated, or may inform the interpretation of a positive or negative result for a given vaccine- or sensitization-indicative antigen. (Notwithstanding the use of the singular form, a vaccine- or sensitization-indicative antigen may be a pool of antigens.)

IDs can include or imply a range of definitional information, or information that otherwise aids the controller or the user. For example, the ID for the test cartridge can include information on the target subjects, such as age, gender, geography and life changing events, or the like, or information on the cartridge manufacture date or expiration, or the like. The ID may include or imply the antigens used, there locations, and the like.

The controller can operate upon reading the IDs to relay the identifying information to the operator. For example, an output screen may announce "A Test Cartridge Infant Immunization Set Has Been Installed. Is This Correct?" A validating response may be required, as inputted by touchscreen, fixed buttons, keyboard, or the like.

Fluidics technology, which at smaller scales can be designated microfluidics technology, has existed for many years with numerous applications including clinical diagnostic devices. Examples include the methods and apparatuses of Kellogg et al., U.S. Pat. No. 7,476,361 (Microfluidics devices and methods of diluting samples and reagents), which include methods and apparatus for performing small-scaled analytic and synthetic procedures. The devices and methods utilize centripetal force resulting from rotation of a platform to motivate fluid movement through channels. Serial dilutions are provided. In another example, Schulte et al., US Patent Application No. 2004/0229378 A1 (Well plate microfluidics), discloses in devices and methods for performing a fluidic processes. The Schulte device includes a well plate comprising a plate and an array of wells formed on or in the plate and a fluidic structure connecting at least two of the wells. The device relies on gravitational and capillary forces that exist in channels within the fluidic structure when receiving fluid streams. Methods and devices for moving fluids with electrodes (electrohydrodynamically) and controlling the flow are described for example in U.S. Pat. Nos. 5,992,820, 6,106,685 and 6,109,717. Microfluidic methods using a pumping fluid to indirectly move fluids with electrodes are described in U.S. Pat. No. 5,961,800 These patent disclosures are incorporated herein in there entirety.

Where fluidic controls, such as electrically operated valves or electrodes, reside in a test cartridge, the cartridge can be adapted to contact electrical leads to the analytical module upon attachment of the cartridge to the module. In certain embodiments, the electrical contacts are located above the fluid moving conduits to minimize fluid contact with the electrical components.

The term dilution refers to the reduction in the amount of a particular subject material per unit volume of a fluid containing that material, through the addition of a second fluid or diluents, which dilution can be conducted serially. The diluent may take on a variety of forms, including aqueous and non-aqueous fluids and may include additional material components such as soluble chemical components or suspensions or emulsions of at least partially insoluble components. The subject material composition including chemical compounds either soluble or as suspensions or emulsions, biological material, either soluble or as a suspensions or emulsions and the like. Serial dilution means successive dilutions where the subject material is diluted with diluent to form a first diluted material, which first diluted material is then diluted with a diluent again, to produce a second diluted material, and so on. For example, one produces a first diluted material that is diluted 1:10 over the subject material. By then diluting at least a portion of this material 1:10, one produces a second dilution material that is a 1:100 dilution of the subject material. In general, the methods, devices and systems of the present invention are useful in subject material greater than 10 fold (1:10), typically greater than 100 fold (1:100), preferably greater than 1000 fold (1:1000) and in many cases, greater than 10,000 fold (1:10,000), within a single integrated microfluidic device, which typically has an integral volume, such as channel volume, of less than 10 ul and preferably less than 1 ul. Serial dilutions can also be made in different scales such as an 8 scale whereby the dilutions would be 1:8, 1:64, 1:512 etc. For example, a microfluidic device can inject 1 volume of the subject material and 7 volumes of diluent to a mixing chamber. Mixing can be by magnetic stirrer, ultrasonic, vortexing of the immunization test cartridge, or the like. From there, 7 volumes are available for the assay, and 1 volume can be injected into a next dilution mixing chamber for the next serial dilution.

The ability to perform serial dilutions using different scales can also enable the production of a customized scale such as 1:10, 1:64, 1:100, 1:512, 1:1000 etc, This is accomplished by selecting the appropriate amount of diluted sample and diluting it with the required amount of diluent. Methods and devices for serial dilutions and controlling the flow are described for example in U.S. Pat. No. 5,869,004, which is incorporated herein in its entirety.

Figures 2, 3:
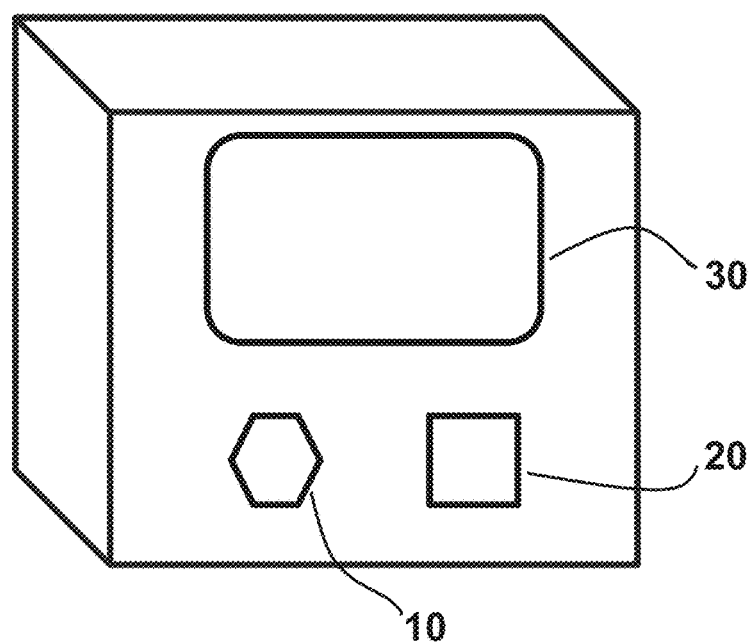
FIG. 2 is a detailed view of the diagnostic assay plate.
FIG. 3 is an overview of the point of care diagnostic device.

FIG. 2 shows a detailed view of an illustrative diagnostic assay plate, which in certain embodiments can be a test cartridge, or incorporated into a test cartridge. The assay plate can be populated with the prescribed dilution pool samples tested against the target antigens. Each well in the assay plate can be populated with equal amounts of antigen from the targeted test cartridge. For example, in the first column, Hep B antigen is present in each well in equal amounts. In certain embodiments, the Hep B antigen is taken from the target test cartridge and distributed in equal amounts into the designated portion of the assay plate. The sample dilutions are also introduced, generally in equal and specified volumes into each well. A color change for example will occur if the antibody is present in sufficient amount in the diluted sample upon binding with the antigen. Next the instruments analyze the sample dilutions that exhibit a signal change and the ones that do not. This data is then used to deduce a dose response curve. The patient's dose response curve is matched against a standard, such as may be designated by a healthcare agency such as the CDC (Centers for Disease Control). If the dose response curve meets the establish standard then no action is needed. If it does not match then the physician may decide to administer a vaccine or vaccine booster per the needs of the patient. This process repeats for each of the antigens in the test cartridge(s). By testing against the recommended panel of target vaccinations a patient will have a complete picture of their immunization profile and how well they are protected against disease. Gaps in the immunization profile can be easily addressed through the administration of the necessary vaccines from the vaccine supply packs.

Biological samples used with the immunization testing device are those that can include antibodies indicative of an immune response in measurable amounts. Often, the biological samples are blood or blood serum, but other biological fluids such as urine or saliva may be used. Biological fluids can be treated to remove larger or higher density elements such as RBCs, lymphocytes or platelets. Such treatment can be by filtration or centrifugation. For blood, an anticoagulant may be used during collection. In certain embodiments, such treatment is done on the immunization testing device with components provided by a biological sample cartridge. Centrifugation can be in-line centrifugation where lower density material flows down the center of a revolving tube. In certain embodiments, there is one biological sample cartridge, which can contain the disposable materials used for pre-dilution sample preparation (if any), dilution buffer, a biological sample acquisition port, sample-handling components used through the dilution stage, and the like. In certain embodiments, the biological sample cartridge is simply a biological sample container, which may connect to plumbing supplied by a test cartridge.

FIG. 3 shows an illustration of the point of care device. It can be a small, compact instrument comprised of for example two ports, one for the blood sample 10 (optional) and one for the targeted test cartridge 20. The shape and color of each port can be unique to prevent switching cartridges and getting an error or damaging the instrument itself. Once both cartridges are inserted properly, the instrument can initiate a pre-run to ensure all elements are present in the proper quantities for the titration assay. When the instrument is ready, a start button (e.g., 40 in FIG. 8) can illuminate indicating to an operator that the instrument is calibrated and everything is in order. The operator then simply presses the start button to commence the assay. Or, the instrument initiates the assay automatically. The results can be displayed in illustrative view screen 30, or transmitted to another device for viewing. The instrument can have connectivity ports to printers and other devices for the transfer of data by wired or wireless means. The data can be used to print results, update a patient's health record or update laboratory/hospital information systems, and the like.

In certain embodiments, the immunization test cartridge is adapted to provide a sample collection feature. For example, it may incorporate a vacutainer, or be adapted to fit a vacutainer (and for example pierce the septum of the vacutainer to draw biological sample into the test cartridge).

The input cartridges can contain circuits that save data on manufacture date or expiration date. Useful circuits include the "Touch Memory" devices from Dallas Semi-Conductors (now a subsidiary of Maxim Integrated Products), which can be adapted to connect by wire or wirelessly to the main instrument upon insertion of the test cartridges. Or, they can contain circuits for monitoring storage conditions, such as temperature. A small power source may be provided on the cartridges to power such monitoring. These circuits are adapted to convey their information to the controller. In certain embodiments, the controller can operate to re-determine an expiration date in view of monitoring data (temperature, humidity, and the like).

Assay detection can be by a single detector (e.g., light absorption detector elements, fluorescence excitation and emission monitoring, and the like) that moves relative to assay sites robotically, is directed to multiple sites with fiber optics, with small-scaled individual detectors, and the like. Or, it can be a CCD or like device that with appropriate lenses monitors all or a useful subset of assay sites simultaneously. Signal can be taken from a liquid phase, or solid phase (assay indicator adsorbed to a surface).

Figure 4:
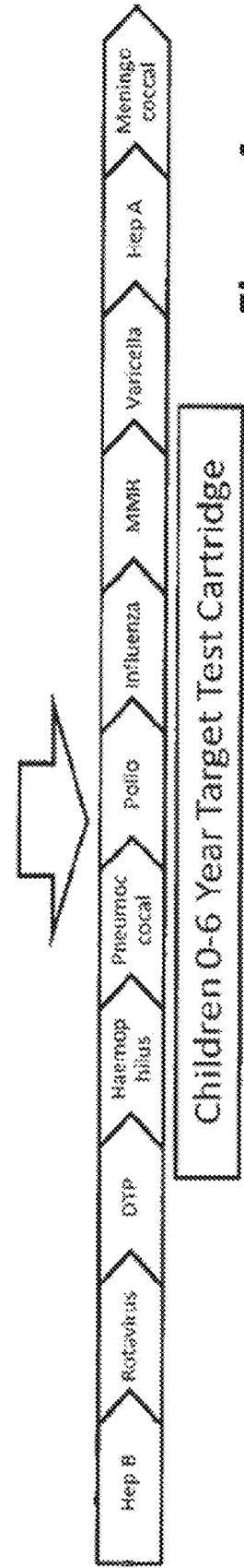
FIG. 4 is a detailed view of a single target test cartridge for infants based upon US Centers for Disease Control guidelines.

FIG. 4 shows an example of an immunization schedule, here provided by the CDC for infants. The targeted test cartridge can be the cognate equivalent of the vaccinations recommended, providing (for example) for reporting in the same order as specified in the table. In this example, eleven tests in the cartridge are housed in the test cartridge. The point of care instrument can distribute for example the specific antigen in equal parts onto assay portion per the assay protocols. The compact, targeted test cartridge can also contain a smart chip which interfaces with the point of care instrument. The smart chip can provide instrument instructions to initiate the proper test protocols, or identify the diagnostic set. The smart chip helps prevent testing errors and minimizes interactions with the operator.

Figure 5:
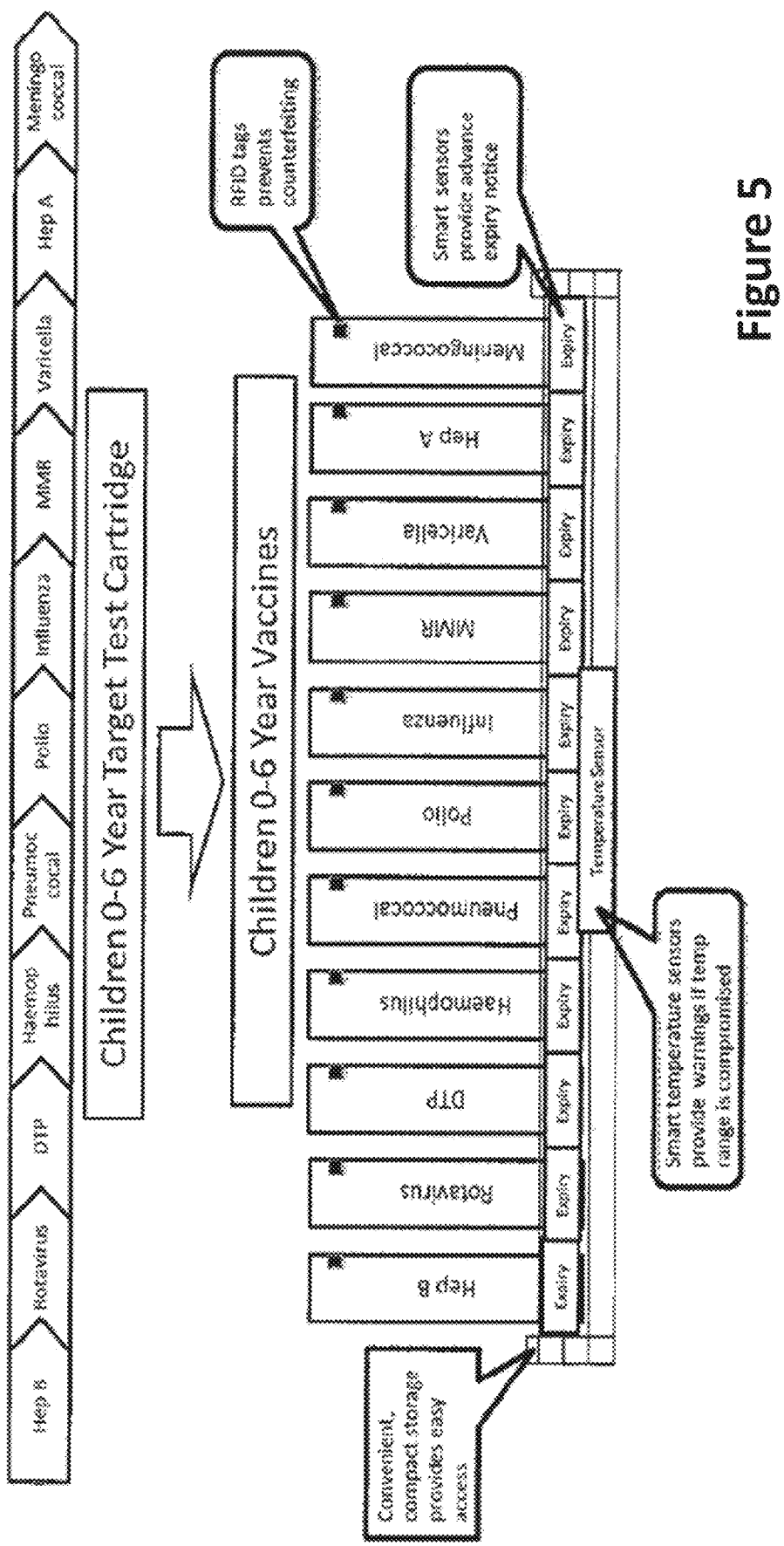
FIG. 5 is a detailed view of an infant vaccine supply pack based upon the corresponding infant target test cartridge.

FIG. 5 shows the vaccine supply pack. The illustration is of the corresponding vaccine supply pack for infants. The vaccines (e.g., in stacks, not shown) are organized in the same sequence as reported in the output when using the infant targeted test cartridge. In the event the test results indicate a deficiency in one or more target vaccinations, the physician can simply take only those appropriate vials to administer the necessary vaccinations. The compact, organized supply pack saves space in the refrigerator and provides easy access. The vaccines can carry a simplified logo (in addition to detailed identifying information) that matches a unique logo used in the reporting of the assay data.

Smart sensors can indicate whether the vaccines have been stored outside the specified temperature range, and for how long. Smart sensors can also indicate whether a vaccine has passed its expiration date. Smart sensors can also indicate vaccine volume and provide advance warning when supply is low. The smart sensors (or connected lighting devices) can illuminate or send a signal providing the clinician advanced warning on the status and viability of the vaccine. The smart tags on each vaccine vial, whether it is a radio frequency or bar code tag, or the like, provides pedigree information to ensure the vaccine has not been compromised or chain of custody has not been broken.

In certain embodiments, the vaccine vials are fitted with IDs (which can include expiration or manufacture date data) and/or temperature monitoring sensors. The IDs can be electronic (though typically there is a printed ID), and these and any monitoring components can be communicated with by a controller (e.g., in the analytical module) wirelessly or via circuits and contacts in the vaccine supply racks. The ID's can be used to confirm that replacement vials are placed in positions that match the order provided in the analysis. In certain embodiments, the vaccine vials are shaped so that the vials can only be placed in supply pack aligned with an ID detector (e.g., bar code detector, short-range RFID reader, or the like).

In certain embodiments, vaccine supply packs are not to have replacement vaccine vials added. Thus, if a vaccine supply pack begins to run out of influenza vaccine, in certain embodiments a replacement supply pack can be ordered that contains more influenza vaccine, and relatively less of less utilized vaccines, as appropriate. Wireless communication can allow the immunization testing device, or another device, to track the inventory, utilizing sensors indicative of the presence of vaccine vials. In certain embodiments, the vaccine supply packs are adapted fit into and electronically connect to a holding rack, which can have the wireless communication hardware.

The immunization testing device or a connected input/output device can be programmed to provide safety controls. For example, a screen can announce that these are the cognate vaccines, identify an indicator of vaccination status associated with the vaccines, and seek input on which vaccines the physician or physician's assistant proposes to administer. The immunization testing device or a connected input/output device can monitor whether the correct vials are pulled (wirelessly), or insist on a validation protocol wherein IDs on the vials are confirmed to match the administration protocol. If the input administration protocol includes vaccines not strongly indicated by the test results, a warning may be outputted.

In certain embodiments, the cartridges, such as test cartridges, provide materials for negative and positive controls. Positive controls can be for example control antibody adapted to react with antigen in the positive control assay regions. Negative controls can be antibody that is not matched to a control antigen. The controller can operate to validate or reject a testing run based on the output from the controls, and can be adapted to retrieve trouble-shooting information based on the circumstances of a rejection.

Larger liquid supplies, such as dilution buffer or buffer for the immune reactions (if different) can be supplied separately from cartridges supplying antigen or the like, such as in cartridge(s) that can be utilized for several runs of the device. Alternatively, all consumables for a given run of the device are provided in a test cartridge.

Figure 8A:
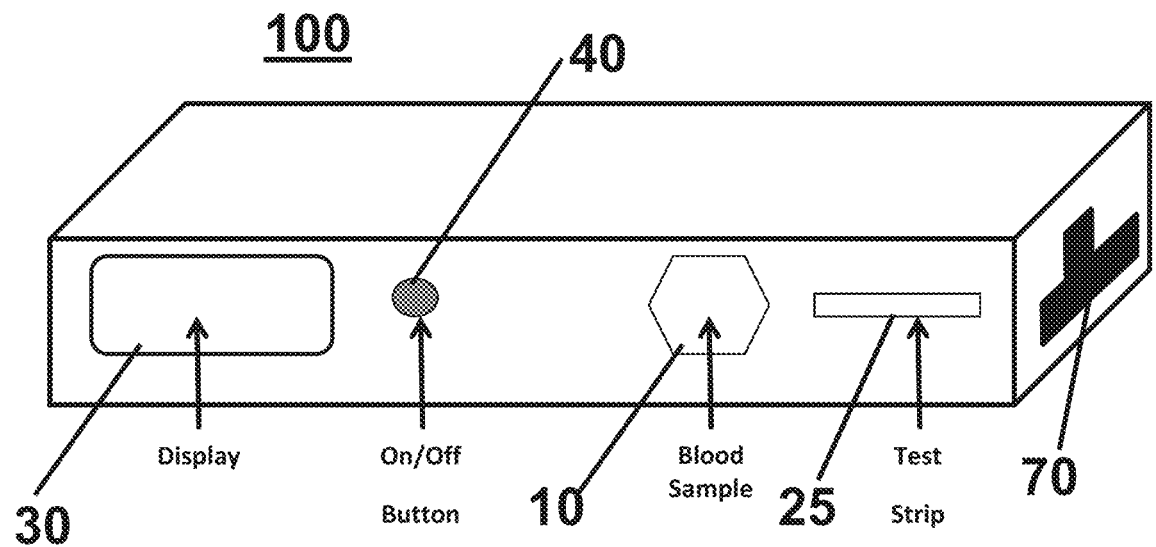
FIGS. 8A, 8B and 8C are overviews of point of care diagnostic devices, some for example using target test strips.

Illustrated in FIG. 8A is a combined immunization pack, immunization composition docking port 70. The port is adapted to fit a pack (e.g., horizontal slot) and an individual immunization composition (e.g., vertical slot) so as to align the IDs thereof for reading by the analytical module, such as by electrical contacts, Bluetooth triggered by appropriate vicinity or fit into the port, RFID triggered by appropriate vicinity, fit into the port, or alignment, bar code reader, or the like.

In certain embodiments, the analytical module weighs 20 pounds or less, or 10 pounds or less (4.536 kg or less), or 5 pounds or less, or 2 pounds or less.

In certain embodiments, the test cartridges contain one or more disease-indicative antigens. These are antigens not supplied in the corresponding vaccine, but which generate antibodies in those exposed to the native causative agent. For example, if a patient is positive for Hep B vaccine antigen and Hep B disease antigen, the physician can deduce that the patient may or may not have been vaccinated, and has probably been exposed to the virus, in which case further analysis for infection may be in order. These can be termed immune reaction source controls.

As tabulated below, the devices and methods of the invention can in certain embodiments

TABLE a. Provide a point of care instrument;
   i. Employ microfluidics for sample and reagent handling;
   ii. Employ micro-titration technology for assays;
   iii. Utilize uniquely (and distinguishably) shaped and/or colored ports;
a. Provide a biological sample cartridge
b. Provide a targeted test cartridge

Figure 7:
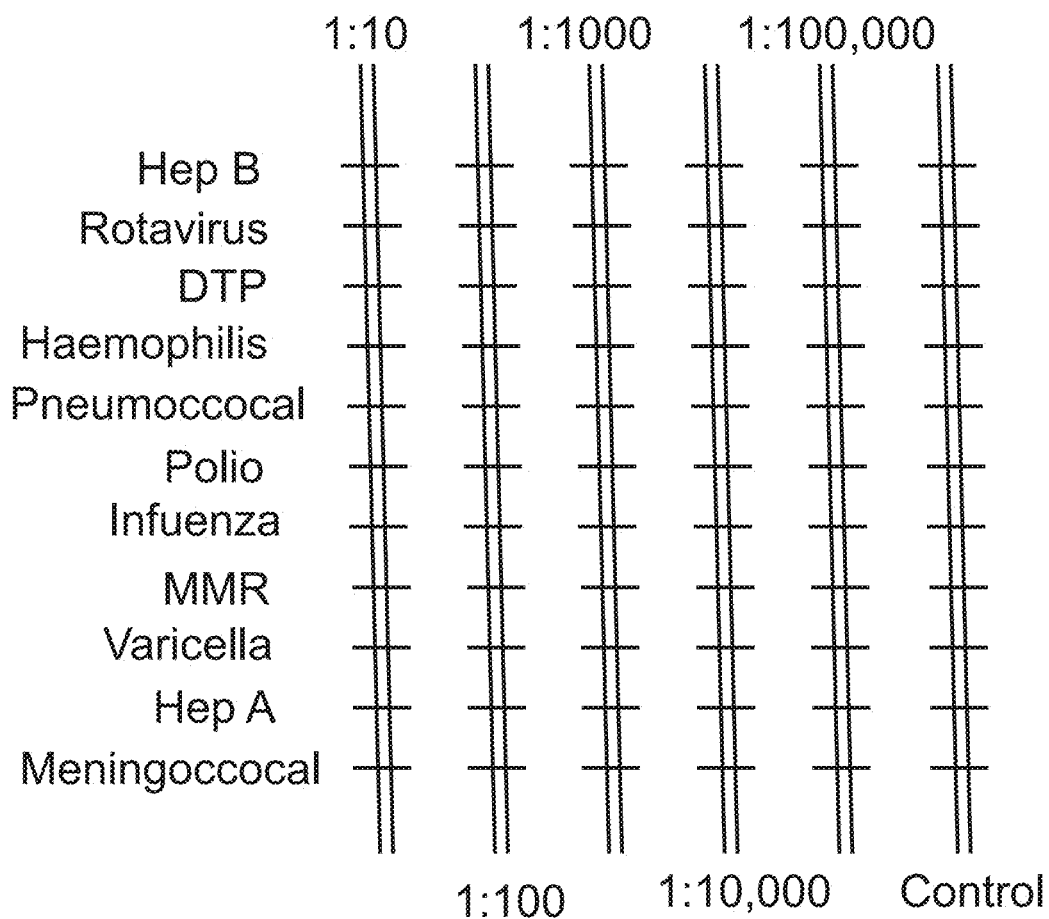
FIG. 7 is a detailed exemplification of a single target test strip for infants based upon US Centers for Disease Control guidelines.

TABLE-continued iv. Utilize a compact, small profile (for the instrument)
v. Provide rapid testing
vi. Utilize AC/DC power sources
vii. Utilize one button operation
viii. Provide low cost
ix. Provide durability
x. Provide wired connectivity
xi. Provide wireless connectivity
xii. Interface with hospital/clinical information systems. Interface with laboratory information systems
b. Provide wired and wireless printer ports
xiii. Provide links to electronic patient records
xiv. Provide self-maintenance (e.g., via diagnostic hardware and software for the instrument and/or the cartridges)
xvii. Provide links to smart phones, PDAs etc.
xviii. Provide biological fluid sample cartridges with
a. Unique shape
b. Distinguishable color
xix. Ability to supply needed sample for assay
xx. Provide targeted test cartridges with
a. Unique shape
b. Distinguishable color
c. Ability to supply needed antigens for assay
d. Chip to instruct instrument to initiate protocols
e. Configured to meet testing requirements as set by healthcare governing bodies
f. Individual chambers for each vaccine target with requisite antigen
xxi. Provide vaccine supply pack with
a. Compact storage for vaccines
b. Easy access
c. Small profile saving space in refrigerator
d. Smart sensors to indicate temperature
e. Smart sensors to indicate expiration date
f. Smart sensors to indicate expiration date
g. Smart sensors to indicate vaccine supply
h. Radio frequency tags to establish pedigree
i. Bar code tags to establish pedigree
xxii. Provide smart app with
a. Smart application for smart phones and computer devices
b. Ability to track and update personal immunization records
c. Ability to share personal immunization records
xxiii. Provide business model for selling vaccines with
a. Companion diagnostic system for vaccines
b. Means for identifying gaps in a person's immunization profile
c. Administering only necessary vaccines
d. Charging a service or handling fee for vaccine administration
e. Charging a fee for the vaccination itself In another embodiment of the invention, the test cartridge incorporates or operates with a test strip (which can be an array of capillaries). The test strip contains the target antigens deposited on the strip. The deposition technology can be printing, lithography, spotting or another method of deposition. The target antigens can be deposited in a series of columns representing different experimental sub-runs, such runs for one or more controls and a number of sample serial dilutions such as 1:10, 1:100, 1:100, etc. Each column has the respective antigen targets such as Hepatitis A, Rotavirus or DTP among other targets (see FIG. 7). The respective diluted sample will be deposited at the top of the column and travel down the designated channel or groove in the test strip. The deposition can contain enough fluid to move the antibodies past all the antigen depositions, or following deposition, sufficient carrier solvent is passed through the strip at the point of sample deposition to move (e.g., by capillary action) the antibodies past all the antigen depositions. The columns of the test strip are fluidically separate such that solvent flowing in one column (e.g., channel) does not carry over to another column.

At each station, the sample encounters a known antigen such as Hepatitis A. If the corresponding antibody is present in the diluted sample a binding event will occur with the target Hepatitis A antigen at the station. The binding reaction would result directly or indirectly in a color, fluorescence, optical density or like change. In certain embodiments, the detectable event is developed by passing developing agents (e.g., labeled anti-human IGG antibodies, enzyme substrates) down the columns in the same manner as used with the sample, or the like.

The remaining sample will travel to the next station, Rotavirus and if the corresponding antibody is present another binding reaction will take place designated by a direct or indirect detectable change. This will continue for all the remaining antigen stations in each column. If the corresponding antibody is not present in the diluted sample then a binding reaction will not occur and a color change (or the like) will not occur. Once all the reactions have taken place for each antigen station in every diluted sample column a number of stations will have changed color. One then would read the results across each target antigen row such as Hepatitis A and plot the results on a dose response curve. If the dose response curve matches the target established by the governing healthcare agency such as the CDC (Centers for Disease Control) in the US then the patient does not need additional vaccinations. If the dose response curves do not match then the patient would be advised by their physician to get a vaccination only for the vaccines that are in question. The establishment of the patient's immunity status is thereby called the immunoprofile. Once the necessary vaccines have been updated the patient's immunoprofile can also be updated and disseminated to medical records, patient records and insurance records among others.

The test strip is configured with the necessary immunization tests per the healthcare guidelines of the specific country for the appropriate group by age, gender and life changing event among others. The test strip 25 can be inserted into the point of care diagnostic instrument (FIGS. 8A and 8B) in the same manner as the aforementioned targeted test cartridge. The blood sample cartridge will remain the same and serve the same function as prior which is to supply the instrument with the patient's blood sample. The blood sample cartridge can have a unique shape from the test strip so as to be differentiated and cannot be mistaken for each other.

Figure 8B:
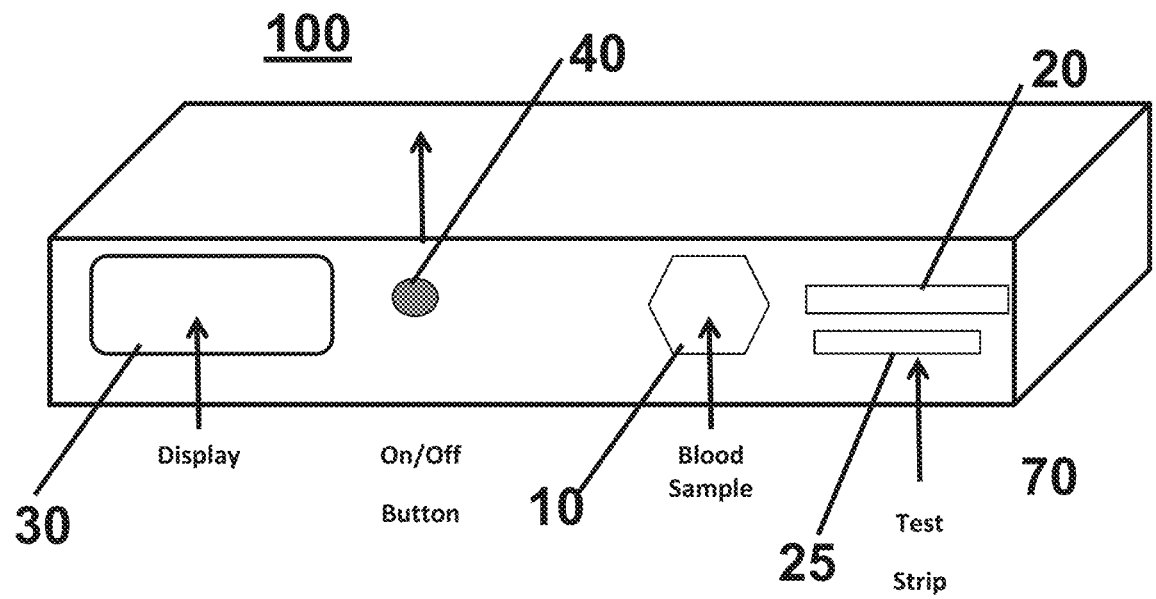
Figure 8C:
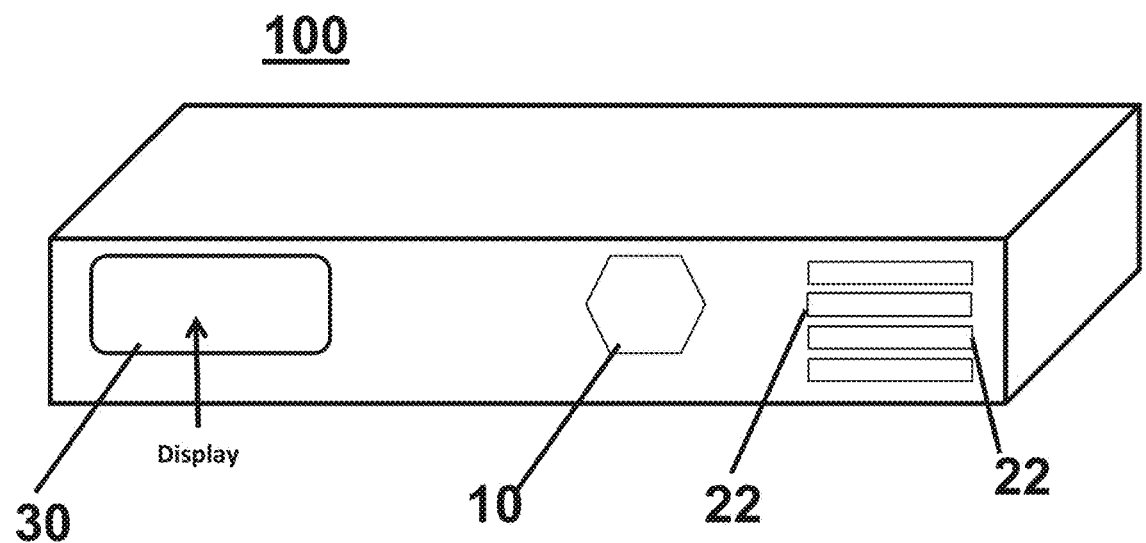

As illustrated in FIG. 8C, there can be multiple items 22, which can be immunization testing cartridges or testing strips or combinations. Similarly, there can be multiple blood sample ports 10—or there can be one or more blood sample ports 10 that shuttle blood sample to multiple items 22. In this way, multiple immunization tests can be conducted from different patients simultaneously, or separate immunization tests for the same patient can be conducted simultaneously.

Figure 9:
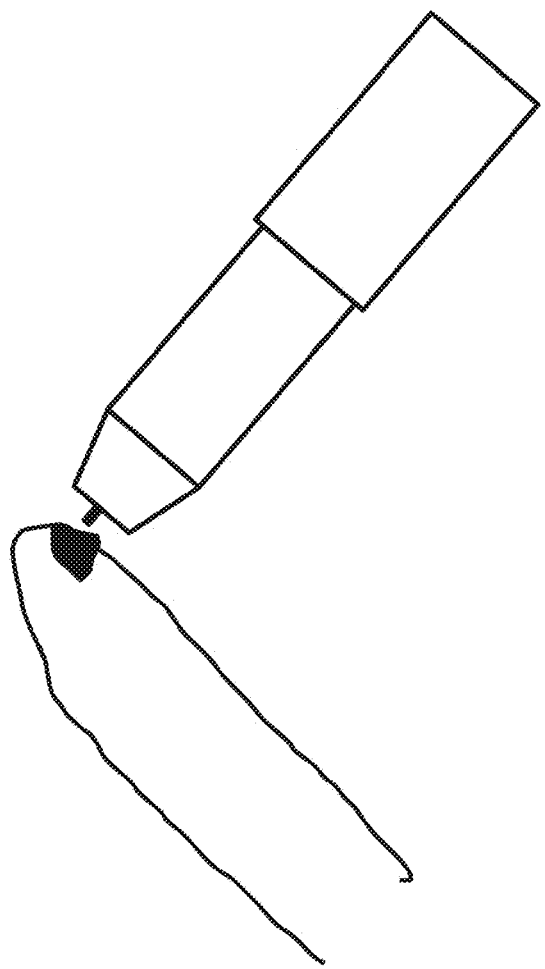
FIG. 9 is an overview of the point of care diagnostic device in the form of a handheld fluid analyzer.

In another embodiment of the invention, the point of care diagnostic instrument is a handheld sampling device which can be a finger prick device (FIG. 9). In this design the sample cartridge is eliminated as the sample is drawn directly from the skin into the device (test cartridge) similar to current blood glucose meters. The sample is prepped as needed using an anti-coagulant to facilitate the serial dilution process described earlier. Once the serial dilution has been complete per the guidelines of the prescribed test, the appropriate dilutions are then assayed. The assay can be via a test strip such as described earlier. For example, the sampling device can incorporate micro-capillaries with the deposited antigens. The hand held version of the point of care instrument would then read the results in the same manner as described above and determine based upon the patient's immunoprofile if any vaccinations are needed to address any identified gaps. Once the necessary vaccines have been updated the patient's immunoprofile can also be updated and disseminated to medical records, patient records and insurance records among others.

Figure 10:
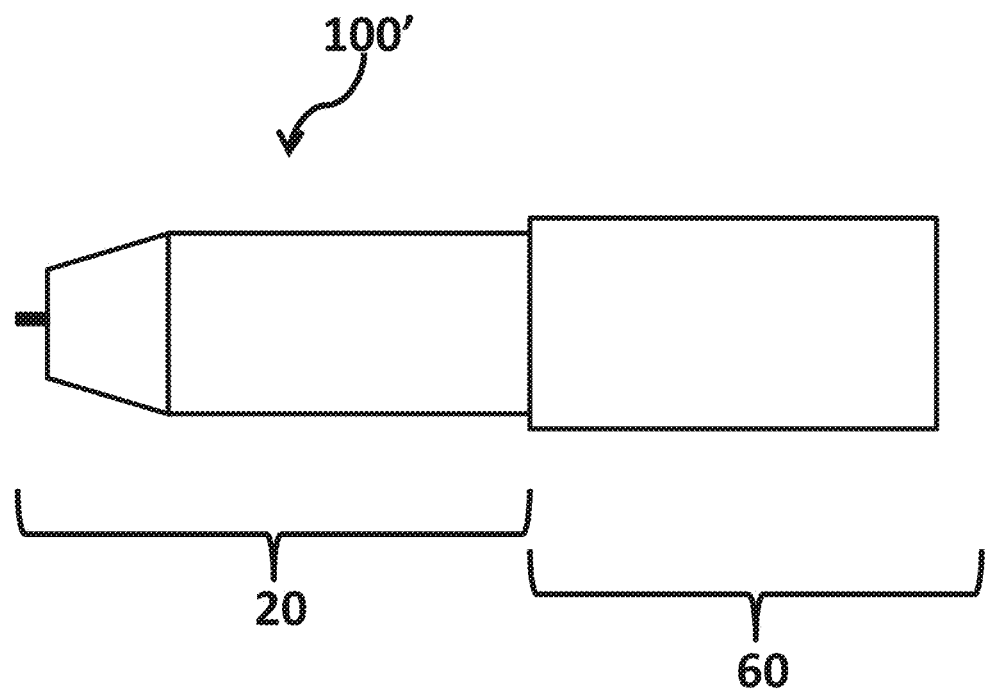
FIG. 10 is an overview of the point of care diagnostic device in the form of a handheld fluid analyzer, with a separable component (here illustrated as a controller).

The handheld sampling device can be reusable with disposable test strips similar to the point of care instrument, or disposable. In one embodiment, a portion comprises the test cartridge 20, and is made up of elements for which it is more economically feasible to dispose on each use, and which includes the fluid-handling components. Electrical, mechanical, fiber optic and the like systems can be comprised within this test cartridge, but more expensive components can be in a separate section, such as controller 50 in the illustration of FIG. 10, which can be reversibly connected to the test cartridge. In certain embodiments, the controller 50 is separate from the test cartridge 20 and connects wirelessly or by wire (e.g., USB, or mini USB).

Figure 11:
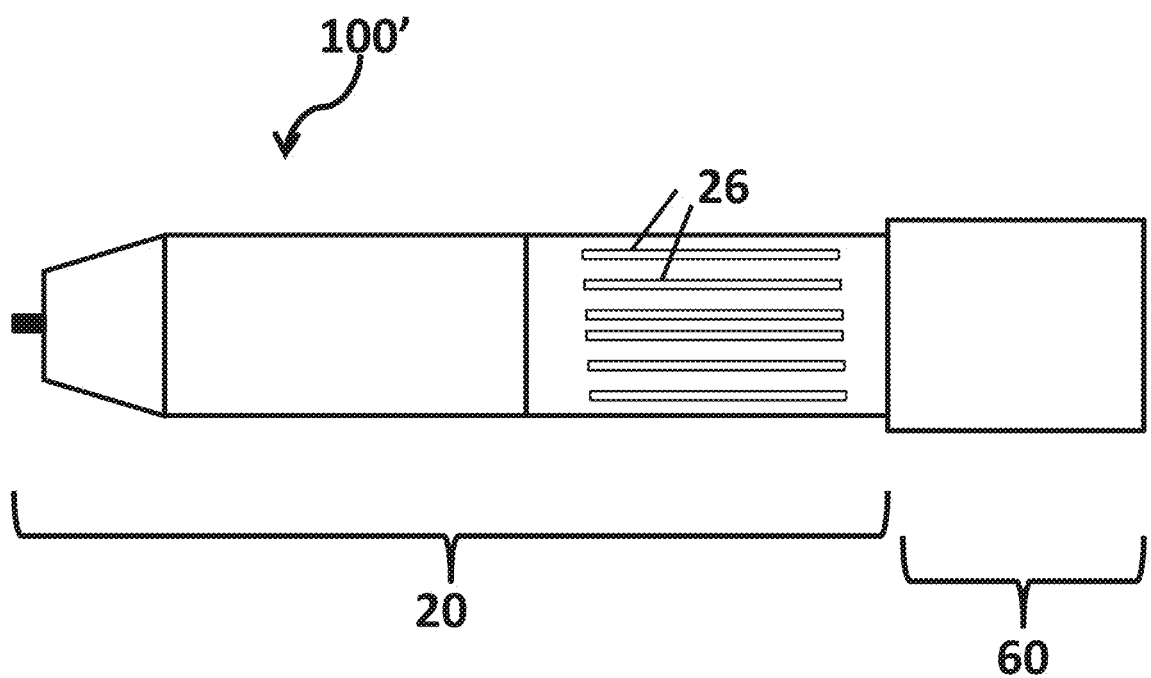
FIG. 11 is an overview of the point of care diagnostic device in the form of a handheld fluid analyzer, with a separable component.

In certain embodiments, the handheld sampling device incorporates viewing windows 26 or the like (FIG. 11) so that the columns of the test strip can be viewed by the user. The windows can have markings to indicate the vaccine antigen alignment, and the various columns (1:1,000; positive control, etc.).

Figure 12:
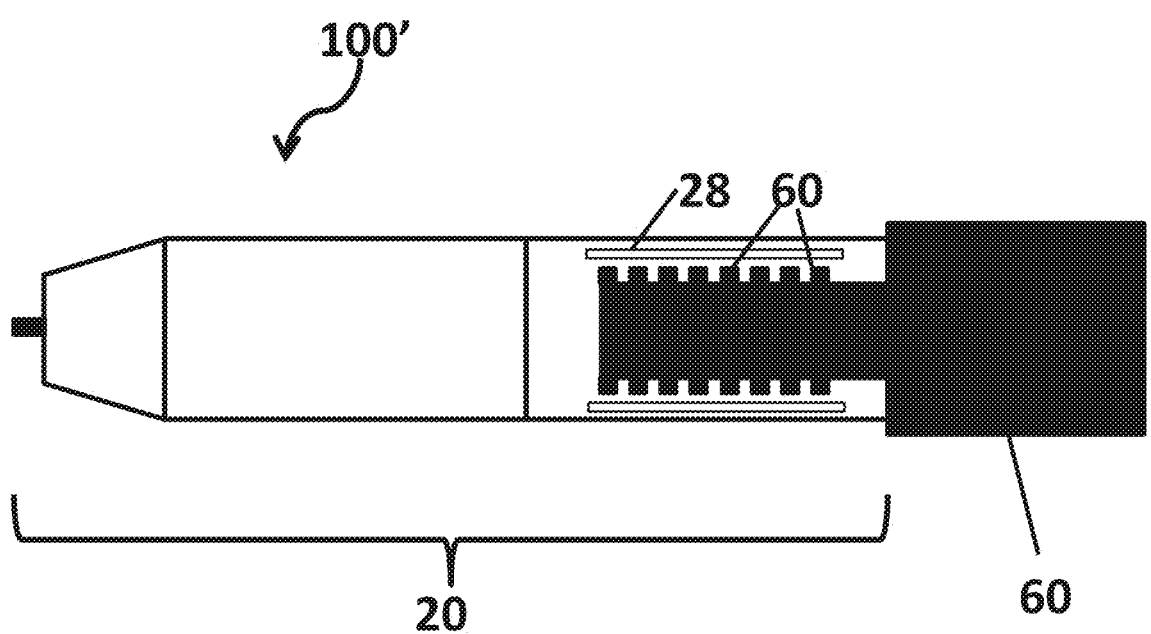
FIG. 12 is a cross-section of the point of care diagnostic device in the form of a handheld fluid analyzer, with a separable component.

In certain embodiments, such as illustrated in the cross-section of FIG. 12, the controller 50 cameras or fiber optic outputs (optical elements) that insert (with fluid segregation) into the test cartridge so that detector elements are not disposable. The optical elements 60 are aligned with the antigen-bound portions of columns 28 of a test strip.

The handheld device is all inclusive able to perform all functions of the point of care instrument. The point of care instrument can also be connected to a computer or the like using for example an USB type connector to transfer and display results. The handheld will also have the same functions as the point of care instrument described earlier but in a portable form to offer convenience and greater value.

It should be noted that the test cartridge illustrated for the handheld fluid sampling device can be the test cartridge utilized in the device of FIG. 3, or of FIG. 8B.

The invention includes methods comprising the functionality described for any embodiment of the testing device or of the periphery devices operative with the testing device.

The immunization testing device can be portable (such as hand-held), or non-portable.

The invention includes the following numbered embodiments:

A. An point-of-care testing device for testing a biological sample from a subject for immunization/sensitization status comprising: ■ an analytical module adapted to make one or two or more dilutions of a fluid that is or is derived from the biological sample, contact said dilutions with separate replicates of vaccine- or sensitization-indicative antigens so as to generate a signals indicative of the amount of antigen-reactive immune molecules in the biological sample dilutions.

B. The immunization testing device of embodiment A for testing a biological sample from a subject comprising, the analytical module comprising ■ a controller, ■ an data output device, and ■ one or more input ports having a conjugate input comprising an immunization test cartridge, wherein the analytical module is adapted to receive an ID from an immunization test cartridge, wherein the controller is adapted to operate the analytical module to make the two or more dilutions of a fluid that is or is derived from the biological sample, contact said dilutions with the separate replicates of vaccine- or sensitization-indicative antigens so as to generate a signals indicative of the amount of antigen-reactive immune molecules in the fluid dilutions, interpret the received ID to identify one of a pre-set plurality of available immunization test cartridges, and to utilize the generated signals and the immunization test cartridge to output a report on the immune status of the subject with respect to an array of separate vaccine- or sensitization-indicative antigens.

C. The immunization testing device of embodiment A or B, wherein any ports present are shaped to accept their conjugate input and not accept the conjugate inputs of other ports present.

D. The immunization testing device of embodiment A, B or C, wherein a controller is adapted to operate with ■ a collection of immunization test cartridges comprising reagents for testing immune status against an array of vaccine- or sensitization-indicative antigens, the collection including two or more cartridges for testing separate arrays of vaccine- or sensitization-indicative antigens, the separate arrays adapted for use with separate patient populations, the cartridges having IDs that are distinctive of the separate arrays, wherein the testing device reads the ID of a given utilized test cartridge and presents an output report correlating the vaccination status results with the respective vaccine- or sensitization-indicative antigens based on the read ID.

E. The immunization testing device of one of the foregoing embodiments, wherein the controller is adapted to operate with ■ packs of immunization compositions, separate packs matching the separate arrays of the immunization test cartridges, the distinct immunization compositions identifiably spatially segregated on the packs, the packs having IDs that are distinctive of the separate arrays of immunization compositions, wherein the immunization testing device comprises an immunization pack ID reader, and wherein after presenting an output report the controller compares the ID of a presented pack with the ID of the utilized test cartridge to confirm that the cognate pack has been presented.

F. The immunization testing device of embodiment one of the foregoing embodiments, wherein the compositions have distinctive IDs, and wherein the immunization testing device comprises an immunization composition ID reader, and wherein after presenting an output report the controller compares an ID of a presented immunization composition with the output report data to confirm that the immunization composition matches the immunization composition called for by the immune status report.

G. The immunization testing device of embodiment one of the foregoing embodiments, wherein the controller is adapted to operate with ■ packs of immunization compositions, separate packs matching the separate arrays of the immunization test cartridges, wherein the immunization testing device comprises an immunization composition ID reader, and wherein after presenting an output report the controller compares an ID of a presented immunization composition with the output report data to confirm that the immunization composition matches the tested vaccine-indicative antigens.

H. The immunization testing device of embodiment F or G, wherein the controller further confirms that the presented immunization composition matches a vaccine-indicative antigen found to have a deficient immune response.

I. The immunization testing device of one of the foregoing embodiments, in the form of a handheld sampling device.

J. The immunization testing device of one of the foregoing embodiments, wherein the vaccine indicative antigens are arrayed on a test strip adapted to contact the dilutions by flow of the dilution material through columns of the test strip so as to serially contact the antigens.

K. The immunization testing device of embodiment J, wherein the test strips are incorporated into the immunization test cartridges.

L. A collection of immunization test cartridges comprising reagents for testing immune status against an array of vaccine- or sensitization-indicative antigens, the collection including two or more cartridges for testing separate arrays of vaccine- or sensitization-indicative antigens, the separate arrays adapted for use with separate patient populations, the cartridges having IDs that are distinctive of the separate arrays.

M. A kit comprising ■ a collection of immunization test cartridges of embodiment L, ■ packs of immunization compositions, separate packs matching the separate arrays of the immunization test cartridges, the distinct immunization compositions identifiably spatially segregated on the packs, the packs having IDs that are distinctive of the separate arrays of immunization compositions, the collections and packs adapted to be operative with an analytical module that utilizes the immunization test cartridges to provide subject immune statuses for the antigens of given immunization test cartridges, and which compares the ID of a utilized immunization test cartridge and that of a presented pack to confirm that the cognate pack has been presented.

N. The kit of embodiment M, wherein the immunization composition packs comprise a temperature sensor, electronic memory for tracking temperature from the sensor over time, and wherein the packs are adapted to communicate the temperature tracking to the analytical module.

O. The kit of embodiment M or N, wherein the immunization test cartridges are in the form of handheld sampling devices.

P. A method of operating the testing device of an embodiment A-K comprising operating the testing device with a biological sample from a patient utilizing an immunization test cartridge, and thereby outputting a report on the immune status of the subject with respect to an array of separate vaccine- or sensitization-indicative antigens.

Q. A method of operating the testing device of an embodiment A-K, comprising ■ operating the testing device with a biological sample from a patient utilizing a said immunization test cartridge, and thereby outputting a report on the immune status of the subject with respect to an array of separate vaccine-indicative antigens; ■ presenting a said immunization pack to the immunization pack ID reader to generate output from the testing device confirming or negating that the immunization pack is the cognate of the test cartridge.

R. The method of embodiment Q, wherein the controller obtains from the immunization pack information on immunization stock, calculates the further utilization implied by the immune status report, and, if needed based on this data, generates (i) a report identifying vaccine restocking needs or (ii) a purchase order to a vaccine supplier.

S. A method of operating the testing device of an embodiment A-K, comprising ■ operating the testing device with a biological sample from a patient utilizing a said immunization test cartridge, and thereby outputting a report on the immune status of the subject with respect to an array of separate vaccine-indicative antigens; and ■ presenting a said immunization composition to the immunization composition ID reader to generate output from the testing device confirming or negating that the immunization composition is the immunization composition called for by the immune status report.

T. A method of operating the testing device of an embodiment A-K, comprising ■ operating the testing device with a biological sample from a patient utilizing a said immunization test cartridge, and thereby outputting a report on the immune status of the subject with respect to an array of separate vaccine-indicative antigens; and ■ presenting a said immunization composition to the immunization composition ID reader to generate output from the testing device confirming or negating that the immunization composition is the immunization composition called for by the immune status report.

U. The method of an embodiment P-T, wherein the analytical module is comprised in a handheld sampling device.

V. The method of an embodiment P-T, where the method is conducted at the point-of-care.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein.

Accordingly, this invention includes all modifications encompassed within the spirit and scope of the invention as defined by the claims that follow.

What is claimed:

1. A method for testing a biological sample from a subject for immunization/sensitization status, the method comprising:
    (a) utilizing an immunization device comprising an analytical module configured to make one or more dilutions of an undiluted fluid that is or is derived from the biological sample, a plurality of separate replicates of different vaccine- or sensitization-indicative antigens so as to generate detectable signals indicative of an amount of antigen-reactive antibodies in the dilutions, corresponding to the different vaccine- or sensitization-indicative antigens and an immunization ID representing established standard levels of antibodies indicative of protective immunization;
    (b) providing the undiluted fluid to the analytical module and selectively having the analytical module conduct the dilutions;
    (c) having the analytical module contact the dilutions with two or more of the plurality of separate replicates of different vaccine- or sensitization- indicative antigens;
    (d) detecting the signals indicative of the amount of antigen-reactive antibodies in the dilutions corresponding to the different vaccine- or sensitization-indicative antigens to establish a dose response curve;
    (e) presenting the immunization ID of established standard levels of antibodies indicative of protective immunization;
    (f) presenting data on immunization/sensitization status of the subject based on step (d);
    (g) comparing the immunization ID of established standard levels of antibodies indicative of protective immunization with the data to identify gaps of immunization/sensitization in the subject relative to the established standard levels of antibodies indicative of protective immunization and to determine vaccine requirements for the subject; and
    (h) outputting a report of the determined vaccine requirements.

2. The method of claim 1, wherein the analytical module further comprises:
    a controller connected to the analytical module;
    a data output device; and
    one or more input ports configured to receive at least one immunization test cartridge wherein the test cartridge has an ID receiver for receiving an ID from an immunization test cartridge, the at least one immunization test cartridge having thereon an array of the plurality of separate replicates of different vaccine- or sensitization-indicative antigens,
    wherein the analytical module is adapted to receive the ID from the at least one immunization test cartridge,
    wherein the controller is adapted to operate the analytical module to (i) make the dilutions of the undiluted fluid that is or is derived from the biological sample, (ii) contact the dilutions with the plurality of separate replicates of different vaccine- or sensitization-indicative antigens disposed in the array of the plurality of separate replicates of different vaccine-or sensitization-indicative antigens so as to generate the signals, (iii) interpret the ID to identify the at least one immunization test cartridge, and (iv) output the report on the immunization/sensitization status of the subject with respect to the array of the plurality of separate replicates of different vaccine- or sensitization-indicative antigens.

3. The method of claim 1, further comprising presenting the immunization ID to an ID reader, and wherein after presenting the report, a controller connected to the analytical module compares with the data from the report.

4. The method of claim 3, further comprising the controller sending an update of a health record of the subject.

5. The method of claim 2, wherein the analytical module is configured to be operative with the at least one immunization test cartridge wherein the vaccine-or sensitization-indicative antigens are arrayed on a test strip contained in the at least one immunization test cartridge.

6. The method of claim 2, wherein the array of the plurality of separate replicates of different vaccine-indicative or sensitization-indicative antigens is disposed on test strips contained in the at least one immunization test cartridge.

7. The method of claim 6, wherein the analytical module contacts the dilutions with the test strips and the dilutions flow through columns of the test strips so as to contact the antigens.

8. The method of claim 7, wherein the analytical module contacts the dilutions with the test strips and the dilutions flow through columns of the test strips so as to serially contact the antigens.

9. The method of claim 2, wherein the separate replicates of different vaccine-indicative or sensitization-indicative antigens are selected from the group consisting of antigens for measles, mumps, rubella, diphtheria, tetanus, pertussis, polio, hepatitis A, hepatitis B, hepatitis C, rotovirus, *haemophilus*, pneumococcal, influenza, varicella and meningococcal.

10. The method of claim 2, wherein the array of the plurality of separate replicates of different vaccine-indicative or sensitization-indicative antigens comprises an array of wells in a plate, the wells containing one of the plurality of separate replicates of different vaccine-indicative or sensitization-indicative antigens.

11. The method of claim 2, wherein the analytical module includes a plurality of input ports, with one of the input ports configured to receive (i) a specimen cartridge containing the undiluted fluid or (ii) the at least one immunization test cartridge.

12. The method of claim 11, wherein one of the input ports is configured to receive the specimen cartridge containing the undiluted fluid.

13. The method of claim 11, wherein the at least one immunization test cartridge includes two or more immunization test cartridges, and wherein two or more of the plurality of input ports are configured to receive the two or more immunization test cartridges.

14. The method of claim 2, wherein the report is output by the data output device, wherein the data output device is selected from the group consisting of a laboratory information system, a medical records system, an electronic patient records system, a smart phone, a PDA, a printer, a tablet and a computer.

15. The method of claim 14, wherein the analytical module outputs the report to the data output device wirelessly.

16. The method of claim 2, wherein the analytical module is configured to be operative with a plurality of different immunization test cartridges, each immunization test cartridge of the plurality of different immunization test cartridges having a distinct array of replicates of vaccine- or sensitization-indicative antigens disposed thereon, and wherein each immunization test cartridge of the plurality of different immunization test cartridges has a distinct ID that is distinctive of the distinct arrays contained thereon, wherein the controller is configured to instruct the analytical module to read the distinct ID of a given immunization test cartridge of the plurality of different immunization test cartridges and present the report to the data output device correlating vaccination status results with the respective vaccine- or sensitization-indicative antigens based on the distinct ID, the method further comprising conducting steps (b) through (d) twice with separate immunization test cartridges, the second conducting done with the same undiluted fluid or a second undiluted fluid and generating one or more reports for the two separate immunization test cartridges.

17. The method of claim 16, wherein the analytical module further comprises an ID reader and the method comprises reading the distinct ID for each immunization test cartridge to identify the distinct array corresponding to the distinct ID.

18. The method of claim 2, wherein the at least one immunization test cartridge contains the undiluted fluid.

19. The method of claim 1, wherein the separate replicates of different vaccine- or sensitization-indicative antigens are selected from the group of antigens consisting of measles, mumps, rubella, diphtheria, tetanus, pertussis, polio, hepatitis A, hepatitis B, hepatitis C, rotovirus, *haemophilus*, pneumococcal, influenza, varicella and meningococcal.

20. The method of claim 1, wherein the analytical module is configured as a handheld sampling device.

21. The method of claim 1, wherein the analytical module is configured as a point of care device.

22. The method of claim 1, wherein the biological sample is blood, sera, lymph fluid, urine, tears, saliva, or a tissue.

* * * * *